(12) United States Patent
Grasdepot

(10) Patent No.: US 6,559,945 B1
(45) Date of Patent: May 6, 2003

(54) METHOD FOR MEASURING SPECTRAL ABSORPTION IN A BODY AND DEVICE THEREFOR

(75) Inventor: François Grasdepot, Fontenay aux Roses (FR)

(73) Assignee: Schlumberger Resource Management Services, Inc.

( * ) Notice: Subject to any disclaimer, the term of this patent is extended or adjusted under 35 U.S.C. 154(b) by 0 days.

(21) Appl. No.: 09/744,646

(22) PCT Filed: Jul. 26, 1999

(86) PCT No.: PCT/EP99/05365
§ 371 (c)(1),
(2), (4) Date: Jan. 27, 2001

(87) PCT Pub. No.: WO00/08442
PCT Pub. Date: Feb. 17, 2000

(30) Foreign Application Priority Data

Aug. 7, 1998 (FR) .......................................... 98 10233

(51) Int. Cl.⁷ ............................................... G01N 21/00
(52) U.S. Cl. ..................................................... 356/432
(58) Field of Search ........................................ 356/432

(56) References Cited

U.S. PATENT DOCUMENTS

| | | | | |
|---|---|---|---|---|
| 4,287,418 A | * | 9/1981 | Divin et al. .............. | 250/336.1 |
| 5,093,576 A | * | 3/1992 | Edmond et al. ......... | 250/370.01 |
| 5,123,733 A | * | 6/1992 | Divin ...................... | 250/336.2 |
| 5,146,092 A | * | 9/1992 | Apperson et al. ........... | 250/343 |
| 5,560,712 A | * | 10/1996 | Kleinerman ................. | 250/330 |
| 5,610,510 A | * | 3/1997 | Boone et al. ............. | 250/336.2 |
| 5,784,158 A | * | 7/1998 | Stanco et al. ................ | 356/326 |
| 5,942,755 A | * | 8/1999 | Dreyer ....................... | 250/343 |
| 6,097,034 A | * | 8/2000 | Weckstrom et al. ......... | 250/343 |
| 6,157,020 A | * | 12/2000 | Krapf et al. ........... | 250/214 LA |
| 6,236,047 B1 | * | 5/2001 | Malin et al. ........... | 250/339.11 |
| 6,340,831 B1 | * | 1/2002 | Kuhara et al. .............. | 257/233 |

OTHER PUBLICATIONS

Kodama, Kazuya, Aizawa, Kiyoharu, Hatori, Mitsutoshi. "Generation of arbitrarily focused images by using multiple differently focused images", *Journal of Electronic Imaging.* Jan. 1998, vol. 7 pp. 138–144.

Burt, Peter and Kolczynski, Raymond. "Enhanced Image Capture Through Fusion", 1993.

* cited by examiner

*Primary Examiner*—John R. Lee
*Assistant Examiner*—Johnnie L Smith, II
(74) *Attorney, Agent, or Firm*—Straub & Pokotylo; Michael P. Straub

(57) ABSTRACT

The spectral absorption of a body, placed between a source for emitting electromagnetic radiation and a detector for detecting the radiation, is measured. The technique includes emitting the electromagnetic radiation in a determined spectral range towards the body, filtering the electromagnetic radiation, and detecting the electromagnetic radiation attenuated by the absorption due to the body and deducing therefrom a measure of the spectral absorption of the body. The filtering and detection steps are implemented by a detector of the quantum type. The technique also applies to determining the calorific value of a gas, for measuring the energy of electromagnetic radiation, and an apparatus for implementing the technique.

29 Claims, 3 Drawing Sheets

METHOD FOR MEASURING SPECTRAL ABSORPTION IN A BODY AND DEVICE THEREFOR

FIELD OF THE INVENTION

The present invention concerns a method of measuring the spectral absorption of a body placed between a source for emitting electromagnetic radiation and a detector for detecting said radiation, the method consisting in performing the following steps:

emitting said electromagnetic radiation in a determined spectral range towards said body;

filtering the electromagnetic radiation; and detecting the electromagnetic radiation attenuated by the absorption due to the body and deducing therefrom a measure of the spectral absorption of said body.

The invention also relates to an apparatus for implementing the method and it applies most particularly to gases.

BACKGROUND OF THE INVENTION

Conventionally, the spectral absorption of a body placed between a source for emitting electromagnetic radiation and a detector of said radiation is measured by:

emitting said electromagnetic radiation in a determined spectral domain by means of an apparatus 10 shown in FIG. 1 and comprising a source 12 and a body 14 that receives the radiation;

filtering the radiation by means of a filter 16, e.g. a filter of the type that is electrically tunable over all or part of the spectral domain under consideration; and detecting the electromagnetic radiation as attenuated by the absorption due to the body by means of a detector 18, and in deducing therefrom a measure of the spectral absorption of said body.

This procedure is applied, for example, to the field of spectroscopy as applied to analyzing gas.

Document EP 0 608 049 illustrates one such example.

To measure the spectral absorption of a body such as a gas, for example, the filtering step makes use either of a plurality of static interference filters each tuned to a narrow range of wavelengths which, once united, cover all or part of the spectral domain under consideration, or else as mentioned above, it makes use of a filter that is tunable over all or part of the spectral domain under consideration.

In the first case, it is necessary to provide a mechanism such as a cylinder, for example, on which the filters are mounted, so that there is only one electromagnetic path, or else to provide a kind of electromagnetic mixer which shares the electromagnetic radiation amongst a plurality of static filters.

With an electromagnetic mixer, is it also necessary to have one detector associated with each filter.

Thus, such a solution is relatively complicated to design and implement and it is costly.

In the second case, the elements of the apparatus are much fewer since a single filter is present and there is only one electromagnetic path to be taken into consideration.

However, it is difficult to find electrically tunable filters in the trade that are suitable for the intended applications, and the design of an electrically tunable filter is no easy task.

Document U.S. Pat. No. 5,703,689 describes apparatus for measuring the spectrum of incident radiation by means of a broad-band optical detector which measures the intensity of incident radiation that has passed through a narrow-band optical element. The band of the optical element can be shifted over a wavelength interval determined by modifying its temperature. The optical element in the form of a semi-conductive film acts as a filter. The spectrum of the incident radiation is obtained by differentiation of the intensity measured by the detector relative to temperature. The filtering and detection steps are thus separate and implemented by two different means, respective optical elements acting as a filter and as a detector.

SUMMARY OF THE INVENTION

From the above it would appear to be advantageous to be able to measure the spectral absorption of a body in a manner that is more simple than in the prior art.

The present invention thus provides a method of measuring the spectral absorption of a body placed between a source for emitting electromagnetic radiation and a detector for detecting said radiation, the method consisting in performing the following steps:

emitting said electromagnetic radiation in a determined spectral range towards said body;

filtering the electromagnetic radiation; and detecting the electromagnetic radiation attenuated by the absorption due to the body and deducing therefrom a measure of the spectral absorption of said body, the method being characterized in that the filtering and detection steps are implemented by a detector of the quantum type.

It is thus no longer necessary to use a filter for the filtering step since the quantum detector itself performs this function, thereby simplifying the measurement technique.

More precisely, the quantum detector presents spectral sensitivity having an absorption front at a given wavelength that corresponds to the bandage of said detector and it delivers a signal corresponding to the electromagnetic energy received by said quantum detector. The method then consists in using the absorption front of the spectral sensitivity of the quantum detector to deduce therefrom the measure of the spectral absorption of the body.

In the invention, the method consists in performing the following steps:

moving the absorption front of the spectral sensitivity of the quantum detector from a position corresponding to a wavelength $\lambda_0$ towards a position corresponding to a wavelength $\lambda_1$, both of which wavelengths are included in the spectral range of the emitted electromagnetic radiation; and combining the signals delivered by the quantum detector for the respective positions of the absorption front corresponding to the wavelengths $\lambda_0$ and $\lambda_1$ and deducing therefrom the measure of the spectral absorption of the body in the wavelength interval lying between $\lambda_0$ and $\lambda_1$.

The term "combining the signals" covers any mathematical operation that puts the signals into a mutual relationship so as to be able to deduce therefrom a measure of the spectral absorption of the body.

For example, the method can consist in taking the difference between signals delivered by the quantum detector for each of the positions of the absorption front corresponding to wavelengths $\lambda_0$ and $\lambda_1$, or in forming the ratio of the signals delivered by the quantum detector for each of the positions of the absorption front corresponding to the wavelengths $\lambda_0$ and $\lambda_0$.

The absorption front of the spectral sensitivity of the quantum detector is obtained by varying a physical parameter on which the position of said absorption front depends.

The invention is of particularly advantageous application when the body is a gas.

In the more particular field of spectroscopy as applied to analyzing gas, the invention also provides a method of determining the calorific value of a gas constituted by fuel components, characterized in that it consists in performing the following steps:

emitting said electromagnetic radiation through said gas in a determined spectral range in which the gas presents absorption;

detecting the electromagnetic radiation attenuated by the absorption due to the fuel components by means of a quantum detector which presents spectral sensitivity having an absorption front corresponding to the bandgap of said detector, while successively moving said absorption front of the detector to positions corresponding to successive wavelengths $\lambda_0, \ldots, \lambda_n$ included in the spectral range, said detector delivering a signal $S(\lambda_i)$ corresponding to the electromagnetic energy received by the quantum detector at each of the positions of the absorption front at wavelength $\lambda_i$;

combining the successive signals delivered by the quantum detector $S(\lambda_i)$, i=0, ..., n so as to isolate the spectral absorption of the fuel components over each wavelength interval $(\lambda_i; \lambda_{i+1})$; and comparing the above-obtained signal combinations with signal combinations previously obtained during a calibration step on a reference gas of known composition, and deducing therefrom the calorific value of the gas.

For example, the method consists in taking the difference $S(\lambda_{i+1})-S(\lambda_i)$ between the signals delivered by the quantum detector for each of the positions of the absorption front corresponding to successive wavelengths $\lambda_0, \ldots, \lambda_n$ taken in consecutive pairs, or in taking the ratio $S(\lambda_{i+1})/S(\lambda_i)$ between signals delivered by the quantum detector for each of the positions of the absorption front corresponding to successive wavelengths $\lambda_0, \ldots, \lambda_n$.

According to a characteristic of the invention, the method consists in moving the absorption front of the spectral sensitivity of the quantum detector by varying a physical parameter on which the position of said absorption front depends.

Another advantageous application lies in the field of measuring the energy of electromagnetic radiation where it can be used, for example, to characterize the emission spectrum of an electromagnetic source.

The invention thus also provides a method of measuring the energy of electromagnetic radiation, the method consisting in performing the following steps:

emitting said electromagnetic radiation in a determined spectral range;

filtering the electromagnetic radiation; and detecting the electromagnetic radiation and deducing therefrom a measure of the energy of said electromagnetic radiation, the method being characterized in that the filtering and detection steps are implemented by a quantum type detector.

More precisely, the quantum detector presents spectral sensitivity having an absorption front at a given wavelength that corresponds to the bandgap of said detector and it delivers a signal corresponding to the electromagnetic energy received by said quantum detector. The method then consists in using the absorption front of the spectral sensitivity of the quantum detector to deduce therefrom the measure of the energy of said electromagnetic radiation.

According to a characteristic, the method consists in performing the following steps:

moving the absorption front of the spectral sensitivity of the quantum detector from a position corresponding to a wavelength $\lambda_0$ to a position corresponding to a wavelength $\lambda_1$ both of which lie in the spectral range of the emitted electromagnetic radiation; and combining the signals delivered by the quantum detector at each of the positions of the absorption front corresponding to the wavelengths $\lambda_0$ and $\lambda_1$ and in deducing therefrom the measure of the energy of the electromagnetic radiation in the wavelength interval lying between $\lambda_0$ and $\lambda_1$.

Thus, by moving the absorption front of the spectral sensitivity of the detector over the entire spectral range under consideration it is possible to reconstitute the emission spectrum of the source over intervals $(\lambda_i;\lambda_{i+1})$.

The method can consist in taking the difference between the signals delivered by the quantum detector for each of the positions of the absorption front corresponding to wavelengths $\lambda_0$ and $\lambda_1$ or indeed in taking the ratio of the signals delivered by the quantum detector for each of the positions of the absorption front corresponding to the wavelengths $\lambda_0$ and $\lambda_1$.

According to a characteristic of the invention, the absorption front of the spectral sensitivity of the quantum detector is moved by varying a physical parameter on which the position of said absorption front depends.

The invention also provides apparatus for measuring the spectral absorption of a body relative to electromagnetic radiation by implementing the corresponding method mentioned above, and comprising:

at least one source for emitting said electromagnetic radiation over a determined spectral range towards said body;

means for filtering said electromagnetic radiation; and means for detecting said electromagnetic radiation and delivering an electrical signal representative of the measure of the spectral absorption of said body, the apparatus being characterized in that the filter means and the detection means are the same means and are constituted by a quantum type detector.

Advantageously, such apparatus is particularly simple in comparison with prior art apparatus since it makes it possible to omit the static interference filters or the electrically tunable filter.

More precisely, the quantum detector presents spectral sensitivity having an absorption front at a given wavelength that corresponds to the bandgap of said detector and it delivers a signal corresponding to the electromagnetic energy received by said quantum detector, and said apparatus further comprises:

means for moving the absorption front of the spectral sensitivity of the quantum detector from a position corresponding to a wavelength $\lambda_0$ towards a position corresponding to a wavelength $\lambda_1$, both of which wavelengths lie in the spectral range of the emitted electromagnetic radiation; and means for combining the signals delivered by the quantum detector for each of the positions of the absorption front corresponding to the wavelengths $\lambda_0$ and $\lambda_1$ and for deducing the measure of the spectral absorption of said body in the wavelength interval lying between $\lambda_0$ and $\lambda_1$.

By way of example, the means for moving the absorption front are constituted by means for varying a physical parameter on which the position of said absorption front depends.

For example, the physical parameter is temperature and the means for varying the temperature of the quantum detector comprise an element powered by a variable electricity source and using Peltier effect junctions with which said quantum detector is maintained in thermal contact, together with a thermometer element associated with said quantum detector.

The means for combining the signals delivered by the quantum detector for each of the positions of the absorption front corresponding to wavelengths $\lambda_0$ and $\lambda_1$ can be constituted by means for taking the difference between said signals or indeed means for taking the ratio of said signals.

By way of example, the body is a gas.

The invention also provides apparatus for determining the calorific value of a gas constituted by fuel components, by implementing the corresponding method stated above and characterized in that it comprises:

at least one source for emitting said electromagnetic radiation through the gas in a determined spectral range in which the gas presents absorption;

means for detecting said electromagnetic radiation attenuated by the absorption due to the fuel components, said means being constituted by a quantum detector presenting spectral sensitivity that has an absorption front corresponding to the bandgap of said detector;

means for moving said absorption front of the spectral sensitivity of the detector to positions corresponding to successive wavelengths $\lambda_0, \ldots, \lambda_n$ included in the determined spectral range, said detector delivering a signal $S(\lambda_i)$ corresponding to the electromagnetic energy received by the quantum detector for each of the positions of the absorption front at a wavelength $\lambda_i$;

means for combining successive signals delivered by the quantum detector $S(\lambda_i)$, i=0, ..., n in such a manner as to isolate the spectral absorption of the fuel components in each wavelength interval $(\lambda_i; \lambda_{i+1})$; and means firstly for comparing the above-obtained signal combinations with signal combinations obtained previously during a calibration step on a reference gas of known composition, and secondly for deducing the calorific value of a gas.

By way of example, the means for moving the absorption front are constituted by means for varying a physical parameter on which the position of said absorption front depends.

By way of example, the physical parameter is temperature and the means for varying the temperature of the quantum detector comprise an element powered by a variable electricity source and using Peltier effect junctions with which said quantum detector is maintained in thermal contact, together with a thermometer element associated with said quantum detector.

The means for combining the signals delivered by the quantum detector for each of the positions of the absorption front corresponding to successive wavelengths $\lambda_0 \ldots, \lambda_n$ can be constituted by means for taking the difference between said signals taken in consecutive pairs $S(\lambda_{i+1})-S(\lambda_i)$ or indeed means for taking the ratio of said signals taken in consecutive pairs $S(\lambda_{i+1})/S(\lambda_i)$.

The invention also provides apparatus for measuring the energy of electromagnetic radiation by implementing the corresponding method mentioned above, and comprising:

at least one source for emitting said electromagnetic radiation over a determined spectral range;

means for filtering said electromagnetic radiation; and means for detecting said electromagnetic radiation and delivering an electrical signal representative of the measure of the energy of said electromagnetic radiation, the apparatus being characterized in that the filter means and the detection means are the same means and are constituted by a quantum type detector.

More precisely, the quantum detector has spectral sensitivity with an absorption front corresponding to the bandgap of said detector for a given wavelength and it delivers a signal corresponding to the electromagnetic energy received by said quantum detector, and said apparatus further comprises:

means for moving the absorption front of the spectral sensitivity of the quantum detector from a position corresponding to a wavelength $\lambda_0$ towards a position corresponding to a wavelength $\lambda_1$, both of which wavelengths are included in the spectral range of the emitted electromagnetic radiation; and means for combining the signals delivered by the quantum detector for each of the positions of the absorption front corresponding to the wavelengths $\lambda_0$ and $\lambda_1$, and for deducing therefrom the measure of the energy of said electromagnetic radiation in the wavelength interval lying between $\lambda_0$ and $\lambda_1$.

By way of example, the means for moving the absorption front can be constituted by means for varying a physical parameter on which the position of said absorption front depends.

By way of example, the physical parameter is temperature and the means for varying the temperature of the quantum detector comprise an element powered by a variable electricity source and using Peltier effect junctions with which the quantum detector is maintained in thermal contact, together with a thermometer element associated with said quantum detector.

BRIEF DESCRIPTION OF THE DRAWINGS

Other characteristics and advantages appear from the following description given purely by way of example and made with reference to the accompanying drawings, in which.

DETAILED DESCRIPTION OF THE DRAWINGS

Figure 1:
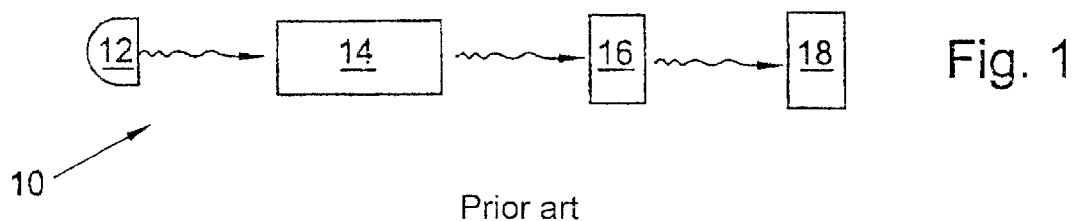
FIG. 1 is a block diagram of prior art apparatus.
Figure 2:
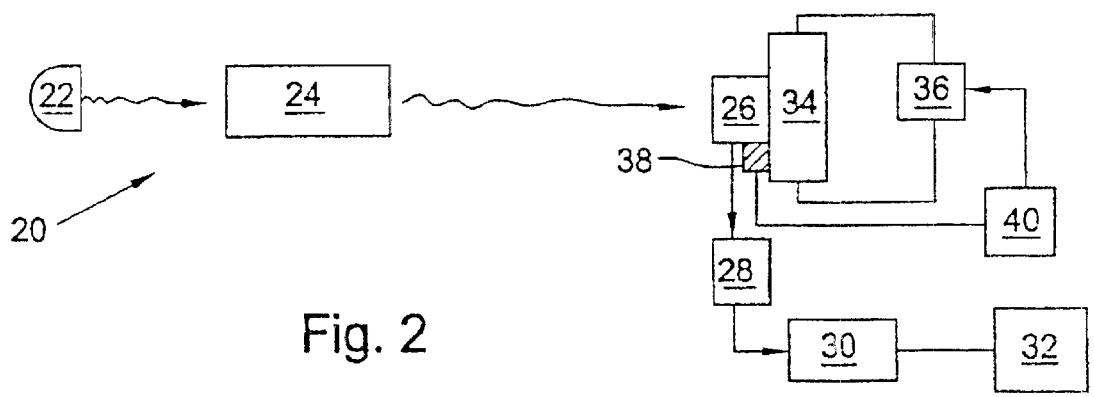
FIG. 2 is a block diagram of apparatus of the invention for measuring the spectral absorption of a gas.

Apparatus for measuring the spectral absorption of a body such as a gas, for example, is shown diagrammatically in FIG. 2 and is given overall reference 20.

The apparatus comprises a source 22 emitting electromagnetic radiation towards the gas which is contained in a cell 24, which radiation is preferably situated in the infrared.

Nevertheless, radiation situated in the visible or in the ultraviolet or indeed in the microwave range or the X-ray range could also be suitable.

By way of example, the infrared radiation source 22 is a broad-band thermal source constituted by a tungsten filament lamp which is spectrally stable for the time required to perform the measurement.

By way of example, it can be a Royal microlamp as sold by Hamai.

The source emits radiation over a spectral range having wavelengths of 0.4 microns ($\mu$m) to 4.2 $\mu$m.

The apparatus also has means for filtering and detecting the radiation which is absorbed in part by the gas in the cell 24, which means are constituted by a quantum type detector 26.

The quantum detector 26 receives the energy contained in the infrared radiation and transforms it into an analog electrical signal representative of said radiation which is in turn transformed into a digital signal by an analog-to-digital converter (ADC) 28 and then injected into a microprocessor 30.

The microprocessor stores the data coming from the detector in a ROM type memory 32.

Figure 4:
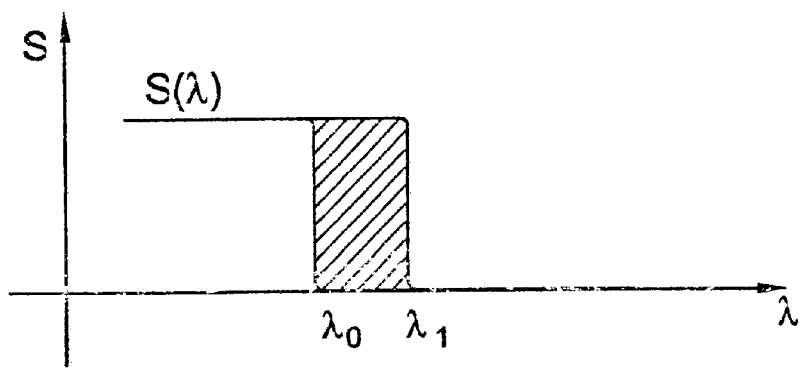
FIG. 4 shows the spectral sensitivity curve of a quantum detector for two different positions of the absorption front.

Such a quantum detector possesses a response or sensitivity that is spectrally variable and which, for increasing wavelengths, appears in the form of a steep flank in the vicinity of a particular wavelength $\lambda_0$ (FIG. 4).

This steep flank is referred to as the "absorption front" in the description below.

The wavelength $\lambda_0$ has a value that is associated with the bandgap E of the electrons in the material constituting the detector, i.e. the energy required to make a transition from an orbital corresponding to energy situated in the valance band of said material to an orbital situated in its conduction band. The relationship between E and $\lambda$ involves the speed of light c and Planck's constant h and it is written $E=hc/\lambda$.

In the vicinity of this bandgap E the absorption of the material, and thus its spectral sensitivity, vary rapidly with wavelength $\lambda_0$ and are highly sensitive to temperature.

As a result, a spectral absorption measurement relying on a quantum detector in a spectral range close to its bandgap is highly unstable with temperature and wavelength.

Consequently, the use of a quantum detector in such a range is avoided when taking accurate spectral absorption measurements.

On the contrary, quantum detectors are generally used in the zone where their spectral sensitivity is essentially flat and their efficiency varies very little as a function of physical parameters such as temperature, pressure, or electric field.

Going against this prejudice, the present invention provides specifically for the absorption front in the spectral sensitivity of a quantum detector to be used for the purpose of deducing a measurement of the absorption or the spectral transmission of the gas in the vicinity of the wavelength corresponding to the bandgap of the detector.

Figure 3:
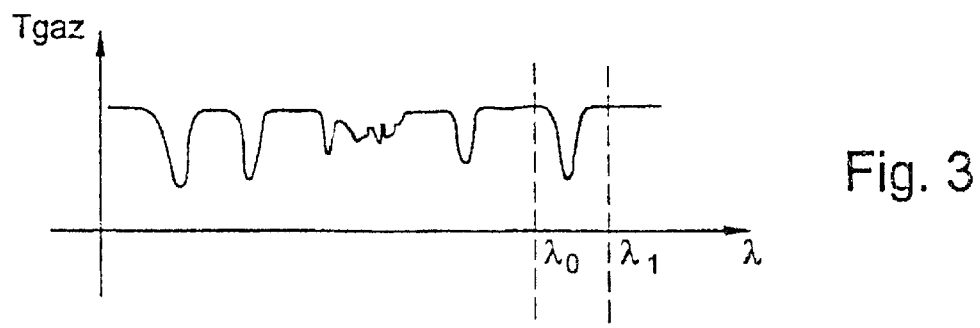
FIG. 3 shows the appearance of the spectral transmission of a gas.

FIG. 3 shows the appearance of the spectral transmission of a gas which shows a notch corresponding to the spectral absorption of the gas between wavelengths $\lambda_0$ and $\lambda_1$, both of which lie in the spectral range emitted by the source, and FIG. 4 shows how the absorption front of the detector is used to isolate this absorption notch in the range of wavelengths under consideration.

By convention, the wavelength corresponding to the bandgap of the detector is taken to be the wavelength that corresponds to the spectrum sensitivity value that is situated at half-height on the curve.

As shown in FIG. 4, the absorption front of the spectral sensitivity of the quantum detector is used in two positions corresponding respectively to the wavelengths $\lambda_0$ and $\lambda_1$ as defined above.

The microprocessor 30 takes the difference between the signals $S(\lambda_0)$ and $S(\lambda_1)$ as provided by the quantum detector 26 in two different positions of the absorption front, and the resulting difference $S(\lambda_i)-S(X_0)$ as represented by shading in FIG. 4 corresponds to the infrared radiation energy received by the detector in the wavelength interval between $\lambda_0$ and $\lambda_1$, said energy being representative of the absorption or spectral transmission of the gas over this range of wavelengths.

It is thus possible to consider this technique for isolating an interval of the spectral range situated between two wavelengths as corresponding to a filtering step performed by means of a tunable filter.

If the signals $S(\lambda_0)$ and $S(\lambda_1)$ are written in the following form:

$$S(\lambda_0)=\int_\lambda E(\lambda)\theta_{gas}(\lambda)\ Sd(\lambda-\lambda_0)d\lambda$$

$$S(\lambda_1)=\int_\lambda E(\lambda)\theta_{gas}(\lambda)\ Sd(\lambda-\lambda_1)d\lambda$$

where:

$E(\lambda)$ designates the light intensity emitted by the source 22;

$\theta_{gas}(\lambda)=\exp(-L\alpha(\lambda))$ designated the spectral response due to the gas at wavelength $\lambda$;

L designates the optical path length through the gas;

$\alpha$ designates the optical absorption coefficient of the gas; and

Figure 5:
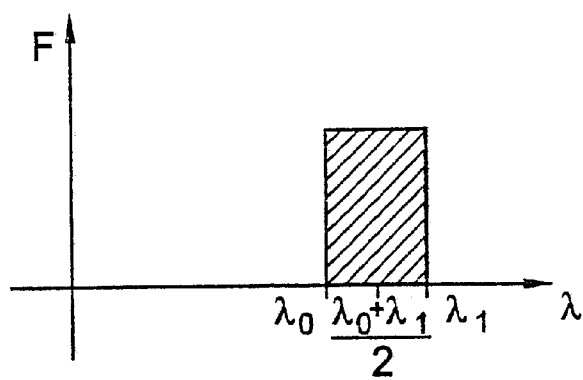
FIG. 5 shows the appearance of the spectral transmission of a tunable filter centered on the wavelength $(\lambda_1+\lambda_0)/2$.

Sd represents the spectral response of the detector; then the difference $S(\lambda_1)-S(\lambda_0)$ can be written:

$$S(\lambda_1)-S(\lambda_0)=\int_\lambda E(\lambda)\theta_{gas}[Sd(\lambda-\lambda_1)-Sd(\lambda-\lambda_0)]d\lambda$$

i.e.

$$\int_\lambda E(\lambda)\theta_{gas}(\lambda)F((\lambda_1+\lambda_0)/2)d\lambda$$

where $F((\lambda_1+\lambda_0)/2)$ designates the spectral transmission of a tunable optical filter centered on the wavelength $(\lambda_1+\lambda_0/2)$, as shown in FIG. 5.

To show up the contribution of the gas between the wavelengths $\lambda_0$ and $\lambda_1$ (FIG. 4) it is also possible to take the ratio $S(\lambda_1)/S(\lambda_0)$ or, more generally, to combine these two signals by means of a mathematical relationship.

The position in terms of $\lambda$ of the absorption front in the spectral sensitivity of the quantum detector depends on physical parameters such as, for example: temperature, pressure, electric field, magnetic field.

The position of the absorption front corresponding to the wavelength $\lambda_1$ (FIG. 4) is obtained by moving the front from its position corresponding to the wavelength $\lambda_0$.

This is done by varying one of the physical parameters mentioned above, e.g. the temperature of the detector.

To do this, the setup shown in FIG. 2 is used that enables the absolute temperature of the quantum detector 26 to be varied.

By way of example, the detector is a photodiode as sold by Hammamatsu under the reference G6890 and it is sensitive in the range 1.1 $\mu$m to 1.6 $\mu$m.

The detector is mounted on an element 34 that is powered by an electricity source 36 and that uses Peltier effect junctions.

The detector is maintained in thermal contact with the element 34 and with a thermometer element 38, e.g. a thermistor associated with said detector. A controller 40 measures the resistance of the thermistor 38, deduces the absolute temperature of the detector therefrom, and controls the injection of a suitable amount of electrical current into the element 34 so as to cause said detector to reach the desired temperature T at which the absorption front is tuned on a particular wavelength.

For this purpose, it should be observed that the relationship $\lambda(T)$ of the material constituting the quantum detector must be known from a prior calibration step.

Thus, for example, it is possible to isolate the contribution of methane gas between wavelengths of 1.60 µm and 1.66 µm by causing the absolute temperature to vary over the range −20° C. to +25° C.

It is also possible to isolate the contribution of water vapor between the wavelengths of 2.6 µm and 2.7 µm by varying temperature over the same range as above but using a quantum detector as sold by Hammamatsu under the reference G6893.

Such apparatus can be used for performing spectral analysis of the gas and can be used as a gas sensor, e.g. for sensing methane, carbon dioxide, or water vapor.

Nevertheless, the apparatus of the invention can also be used to measure the spectral absorption of bodies such as water and liquid hydrocarbons, for example.

Figure 6:
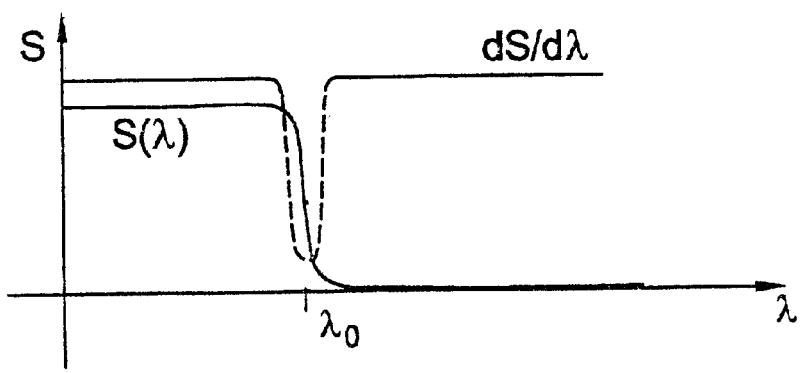
FIG. 6 shows the spectral sensitivity of a quantum detector and its derivative relative to wavelength.

It will be observed that the derivative of the sensitivity S of the detector relative to wavelength $\lambda$ (shown in FIG. 6) corresponds to the notch type spectral transmission of an optical filter.

It will thus be understood that by differentiating the spectral sensitivity of the detector relative to $\lambda$ or by moving the absorption front of the spectral sensitivity of the detector, amounts to performing the function that is exercised by a tunable optical filter.

When $\lambda_1 = \lambda_0 + \Delta\lambda$, which corresponds to a small change in wavelength $\Delta\lambda$, the fact of taking the difference $S(\lambda_0 + \Delta\lambda) - S(\lambda_0)$ amounts, so to speak, to differentiating the signal S in the vicinity of $\lambda_0$ to within $\Delta\lambda$.

Figure 7:
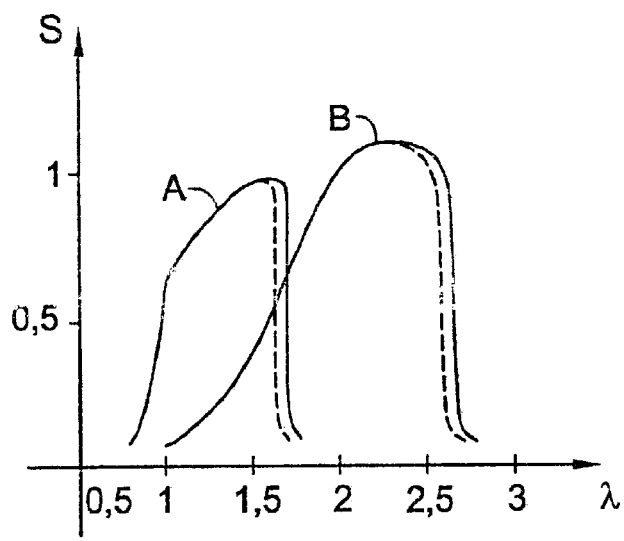
FIG. 7 shows curves A and B representing the spectral sensitivity of quantum detectors having the references G6890 and G6893 respectively as sold by Hammamatsu.

FIG. 7 shows the wavelength sensitivity curves A and B of the detectors mentioned above under the references G6890 and G6893, respectively. The dashed-line portions and continuous-line portions of the absorption front correspond respectively to a temperature of −20° C. and to a temperature of +25° C.

In a second application, it is advantageous to use the apparatus of the invention to determine the calorific value of natural gas which is made up of fuel components.

Figure 8:
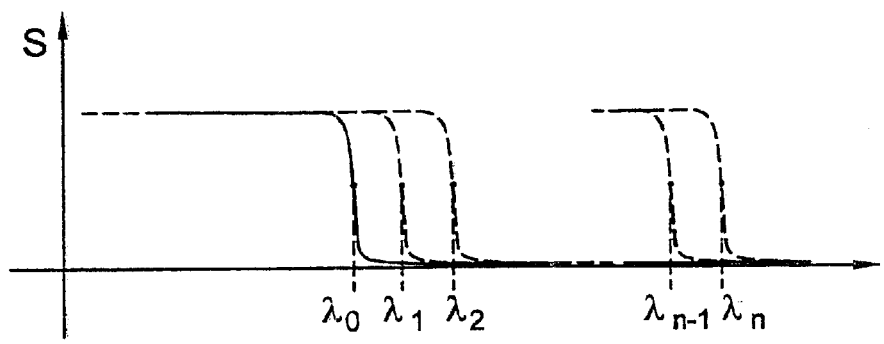
FIG. 8 shows the spectral sensitivity of a quantum detector at various different positions of the absorption front.

For this purpose, the apparatus shown in FIG. 2 is retained with the cell 24 being filled with natural gas, and a physical parameter on which the position of the absorption front of the quantum detector 26 is varied, e.g. the absolute temperature of the detector, over a range of temperatures thus enabling the absorption front to move over wavelengths $\lambda_0$, $\lambda_1, \lambda_2, \ldots, \lambda_{n-1}, \lambda_n$ (FIG. 8).

For each of the positions of the absorption front corresponding to a wavelength $\lambda_i$, the detector delivers a signal $S(\lambda_i)$ which is stored in the memory 32 and thereafter the microprocessor 30 takes the differences between consecutive signals $S(\lambda_{i+1}) - S(\lambda_i)$ for i=0, . . . , n or else it takes the ratios of the signals $S(\lambda_{i+1})/S(\lambda_i)$ or it performs some other mathematical combination associating these signals so as to isolate the contribution of the gas in each of the intervals ($\lambda_i$; $\lambda_{i+1}$) and deduce therefrom a value for the absorption or spectral transmission of the gas in said interval.

By comparing signals $S(\lambda_{i+1}) - S(\lambda_i)$ with reference signals $(S(\lambda_{i+1}) - S(\lambda_i))$ref obtained previously during a calibration step implemented on a reference gas of known composition, it is possible to deduce the calorific value of the natural gas in question.

For example, natural gas possesses the following composition:

methane: 89.5%
ethane: 5%
propane: 1%
butane: 0.6%
pentane: 0.3%
inert gases: 3.6%

A plurality of wavelengths $\lambda_0$ to $\lambda_5$ (n=5) are used to determine the contributions of the various components of the above-mentioned natural gas with the exception of the inert gases which do not make any contribution to calorific value.

These wavelengths are such that each of them corresponds to the contribution of a plurality of fuel components.

By applying various temperatures to the detector by means of the setup shown in FIG. 2, the absorption front of the spectral sensitivity of said detector is tuned over respective wavelengths in the range $\lambda_0$ to $\lambda_5$.

For each position $\lambda(T)$, the quantum detector 26 delivers an electrical signal corresponding to $S(\lambda)$:

$$S(\lambda_0) = \int_\lambda E(\lambda) \theta_{gas}(\lambda, x_i) \, Sd(\lambda - \lambda_0) d\lambda$$

where $E(\lambda)$ designates the light intensity emitted by the source 22, $$\theta_{gas}(\lambda, x_i) = \exp\left(-L \times \sum_i \alpha_i(\lambda) \times x_i\right)$$

designates the spectral response due to all of the gaseous fuel components present at said wavelength;

L designates the optical path length through the gas;

$x_i$ represents the number of moles of fuel component i per unit volume at pressure P and temperature T;

$\alpha_i$ designates the absorption coefficient of fuel component i, which depends on wavelength, pressure, and temperature; and Sd represents the spectral response of the detector.

By taking the differences $S(\lambda_{i+1}) - S(\lambda_i)$ for consecutive pairs of wavelengths $\lambda_0, \lambda_1, \ldots, \lambda_5$, five values are obtained for which absorbance A is defined as follows:

$$A(\lambda_i; \lambda_{i+1}) = Ln(1/(S(\lambda_{i+1}) - S(\lambda_i)))$$

where Ln designates the natural logarithm function, and the following system of five equations is obtained:

$$A_1 = a_{11}x_1 + a_{21}x_2 + \ldots + a_{51}x_5$$

$$A_2 = a_{12}x_1 + a_{22}x_2 + \ldots + a_{52}x_5$$

$$A_5 = a_{15}x_1 + a_{25}x_2 + \ldots + a_{55}x_5$$

where the terms $a_{ij}$ depend on the component i and on the apparatus 20.

Before implementing the invention on a natural gas of unknown composition, an initial calibration step is performed in the laboratory during which various gases are injected into the apparatus 20, said gases having components $x_i$ for which the numbers of moles per unit volume are known at given T and P.

The calibration step is usually performed by means of a Fourier transform spectrometer.

For a mixture of known fuel components, by tuning the absorption front of the spectral sensitivity of the quantum detector 26 over the wavelengths $\lambda_0, \lambda_1, \ldots, \lambda_5$, a system of five equations is obtained:

$$A_{11} = a_{11}x_1 + \ldots + a_{51}x_5$$

$$A_{51} = a_{15}x_1 + \ldots + a_{55}x_5$$

where the $x_i (i=1, \ldots, 5)$ are known and where the terms $a_{ij}$ are unknown.

By injecting four other known gas mixtures into the apparatus 10, twenty additional equations are obtained having the same terms $a_{ij}$ as before.

This makes it possible using conventional mathematics, e.g. a method of resolving linear equations, to calculate the coefficients $a_{ij}$ which are defined as follows:

$$[A_j]_{k=1,\ldots,5} = [a_{ij}] \, [x_j]_{k=1,\ldots,5}$$

where the indices k identify the particular known gas mixture.

By inverting the matrix $[a_{ij}]$ using a conventional mathematical inversion method, a system of equations is obtained as follows:

$$[x_i]_{x=1,\ldots,5} = [a_{ij}]^{-1}_{\substack{i=1,\ldots,5 \\ j=1,\ldots,5}} [A_j]_{i=1,\ldots,5} = [b_{ij}]_{\substack{i=1,\ldots,5 \\ j=1,\ldots,5}} [A_j]_{i=1,\ldots,5}$$

Thus, the values of $x_i$ are written:

$$x_i = \sum_{j=1,\ldots,5} b_{ij} \times A_j x_i = \sum b_{ij} A_j$$

It suffices to use the memory 32 to store the data $b_{ij}$ as calculated during calibration and then when dealing with a natural gas of unknown composition and thus of unknown calorific value, various values $A_j$ are measured for different intervals $[\lambda_i; \lambda_{i+1}]$ obtained as described above, and the terms $x_i$ are easily deduced therefrom.

The calorific value H(P,T) of a gas is written:

$$\sum_{i=1,\ldots,5} x_i \times H_i$$

where $H_i$ represents the calorific value of component i in Joules per mole.

Consequently, once the terms $x_i$ have been determined, the calorific value H(P,T) can be obtained directly.

Figure 9:
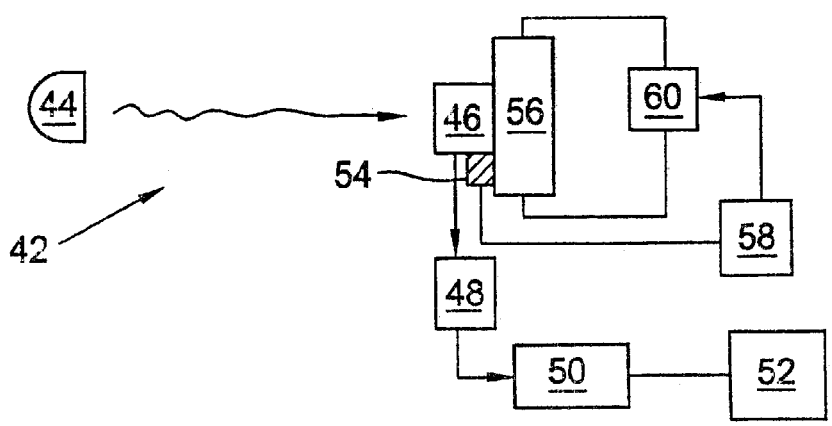
FIG. 9 is a diagram of apparatus of the invention for measuring the energy of electromagnetic radiation.

In another particularly advantageous application, FIG. 9 is a diagram of apparatus 42 for measuring the energy of electromagnetic radiation emitted by a source 44 in a determined spectral range and received by a quantum detector 46.

In a manner identical to that described above with reference to FIG. 2, the electrical signal provided by the detector is converted into a digital signal by the converter 48 and processed by the microprocessor 50, a memory 52 of the ROM type being used to store the data coming from the detector and the microprocessor.

The setup constituted by a thermistor 54 associated with the detector 46, the element 56 provided with Peltier effect junctions, the controller 58, had the electricity source 60 is identical both structurally and functionally to that shown in FIG. 2.

Thus, by moving the absorption front of the spectral sensitivity of the detector over the entire spectral range of the source 44, it is possible to reconstitute its emission spectrum in wavelength intervals $(\lambda_i; \lambda_{i+1})$.

What is claimed is:

1. A method of measuring the spectral absorption of a body placed between a source for emitting electromagnetic radiation and a detector for detecting said radiation, the method comprising the following steps:

emitting said electromagnetic radiation in a determined spectral range towards said body;

filtering the electromagnetic radiation; and detecting the electromagnetic radiation attenuated by the absorption due the body and deducing therefrom a measure of the spectral absorption of said body, the filtering, and detection steps being combined and implemented by a quantum type detector which presents spectral sensitivity having an absorption front at a given wavelength that corresponds to the bandgap of said detector and delivers a signal corresponding to the electromagnetic energy received by said quantum detector, said method including using the absorption front of the spectral sensitivity of the quantum detector to deduce therefrom the measure of the spectral absorption of the body.

2. A method according to claim 1, further comprising:

moving the absorption front of the spectral sensitivity of the quantum detector from a position corresponding to a wavelength $\lambda_0$ towards a position corresponding to a wavelength $\lambda_1$, both of which wavelengths are included in the spectral range of the emitted electromagnetic radiation; and combining the signals delivered by the quantum detector for the respective positions of the absorption front corresponding to the wavelengths $\lambda_0$ and $\lambda_1$ and deducing therefrom the measure of the spectral absorption of the body in the wavelength interval lying between $\lambda_0$ and $\lambda_1$.

3. A method according to claim 2, further comprising; taking the difference between the signals delivered by the quantum detector for each of the positions of the absorption front corresponding to the wavelengths $\lambda_0$ and $\lambda_1$.

4. A method according to claim 2, further comprising: taking the ratio of the signals delivered by the quantum detector for each of the positions of the absorption front corresponding to the wavelengths $\lambda_0$ and $\lambda_1$.

5. A method according to any one of claims 2 to 4, wherein moving the absorption front of the spectral sensitivity of the quantum detector includes varying a physical parameter on which the position of said absorption front depends.

6. Application of the method according to claim 1, in which said body is a gas.

7. A method of determining the calorific value of a gas including fuel components, the method comprising:

emitting said electromagnetic radiation through said gas in a determined spectral range in which the gas presents absorption;

filtering the electromagnetic radiation; and detecting the electromagnetic radiation attenuated by the absorption due to the fuel components, said filtering and detection steps being combined and implemented by a quantum type detector which presents spectral sensitivity having an absorption from corresponding to the bandgap of said detector, while successively moving said absorption front of the detector to positions corresponding to successive wavelengths $\lambda_0, \ldots, \lambda_n$ included is in the spectral range, said detector delivering a signal $S(\lambda_i)$ corresponding to the electromagnetic energy received by the quantum detector at each of the position of the absorption front at wavelength $\lambda_i$;

combining the successive signals delivered by the quantum detector $S(\lambda_i)$, i=0, . . . , n so as to isolate the spectral absorption of fuel components over each wavelength interval $(\lambda_i; \lambda_{i+1})$; and comparing the above obtained signal combinations with signal combinations previously obtained during a calibration step on a reference gas of known composition, and deducing therefrom the calorific value of the gas.

8. A method according to claim 7, further comprising:

taking the difference $S(\lambda_{i+1})-S(\lambda_i)$ between the signals delivered by the quantum detector at each of the positions of the absorption front corresponding to the successive wavelengths $\lambda_0, \ldots \lambda_n$, taken in consecutive pairs.

9. A method according to claim 7, further comprising:

taking the ratio $S(\lambda_{i+1})/S(\lambda_i)$ of the signals delivered by the quantum detector at each of the positions of the absorption front corresponding to the successive wavelengths.

10. A method according to any one of claims 7 to 9, wherein moving the absorption front of the the quantum detector includes varying a physical parameter on which the position of said absorption front depends.

11. A method of measuring the energy of electromagnetic radiation, the method comprising:

emitting said electromagnetic radiation in a determined spectral range;

filtering the electromagnetic radiation; and detecting the electromagnetic radiation and deducing therefrom a measure of the energy of said electromagnetic radiation, the filtering and detection steps being combined and implemented by a quantum type detector which presents special sensitivity having an absorption front at a given wavelength that corresponds to the bandgap of said detector and delivering a signal corresponding to the electromagnetic energy received by said quantum detector, the method including using the absorption front of the spectral sensitivity of the quantum detector to deduce therefrom the measure of the energy of said electromagnetic radiation.

12. A method according to claim 11, comprising:

moving the absorption front of the spectral sensitivity of the quantum detector from a position corresponding to a wavelength $\lambda_0$ to a position corresponding to wavelength $\lambda_1$ both of which lie in the spectral range of the emitted electromagnetic radiation; and combining the signals delivered by the quantum detector at each of the positions of the absorption front corresponding to the wavelengths $\lambda_0$ and $\lambda_1$ and in deducing therefrom the measure of the energy of the electromagnetic radiation in the wavelength interval lying between $\lambda_0$ and $\lambda_1$.

13. A method according to claim 12, further comprising; taking the difference between the signals delivered by the quantum detector at the positions of the absorption front corresponding to the wavelengths $\lambda_0$ and $\lambda_1$ respectively.

14. A method according to claim 12, further comprising: taking the ratio of the signals delivered by the quantum detector for each of the positions of the absorption front corresponding to the wavelengths $\lambda_0$ and $\lambda_1$ respectively.

15. A method according to any one of claims 12 to 14, wherein moving the absorption front of the spectral sensitivity of the quantum detector includes varying a physical parameter on which the position of said absorption front depends.

16. Apparatus for measuring the spectral absorption of a body relative to electromagnetic radiation to implement the method according to claim 1 the apparatus comprising:

at least one source for emitting said electromagnetic radiation over a determined spectral range towards said body;

a quantum type detector for filtering said electromagnetic radiation and for detecting said electromagnetic radiation and delivering an electrical signal representative of the measure of the spectral absorption of said body.

17. Apparatus according to claim 16, in which the quantum detector presents spectral sensitivity having an absorption front at a given wavelength that corresponds to the bandgap of said detector and delivering a signal corresponding to the electromagnetic energy received by said quantum detector, said apparatus further comprising:

means for moving the absorption front of the spectral sensitivity of the quantum detector from a position corresponding to a wavelength $\lambda_0$ towards a position corresponding to a wavelength $\lambda_1$, both of which wavelengths lie in the spectral range of the emitted electromagnetic radiation; and means for combining the signals delivered by the quantum detector for each of the positions of the absorption front corresponding to the wavelengths $\lambda_0$ and $\lambda_1$ and for deducing the measure of the spectral absorption of said body in the wavelength interval lying between $\lambda_0$ and $\lambda_1$.

18. Apparatus according to claim 17, in which the means for moving the absorption front include means for varying a physical parameter on which the position of said absorption front depends.

19. Apparatus according to claim 18, in which the physical parameter is temperature and the means for varying the temperature of the quantum detector includes an element powered by a variable electricity source and using Peltier effect junctions with which said quantum detector is maintained in thermal contact together with a thermometer element associated with said quantum detector.

20. Apparatus according to claim 17, in which the means for combining the signals delivered by the quantum detector at each of the positions of the absorption front corresponding to the wavelengths $\lambda_0$ and $\lambda_1$ are constituted by means for taking the difference between said signals.

21. Apparatus according to claim 17, in which the means for combining the signals delivered by the quantum detector at each of the positions of the absorption front corresponding to the wavelengths $\lambda_0$ and $\lambda_1$ are constituted by means for taking the ratio of said signals.

22. The use of the apparatus according to any one of claims 16 to 21, in which the body is a gas.

23. Apparatus for determining the calorific value of a gas constituted by fuel components, by implementing the method according to any one of claims 7 to 9, the apparatus comprising:

at least one source for emitting said electromagnetic radiation through the gas in a determined spectral range in which the gas presents absorption;

a quantum detector presenting spectral sensitivity that has an absorption front corresponding to the bandgap of said detector for filtering said electromagnetic radiation and for detecting said electromagnetic radiation attenuated by the absorption due to the fuel components;

means for moving said absorption front of the spectral sensitivity of the detector to positions corresponding to successive wavelengths $\lambda_0, \ldots, \lambda_n$ included in the determined spectral range, said detector delivering a signal S ($\lambda_i$) corresponding to the electromagnetic energy received by the quantum detector for each of the positions of the absorption front at wavelength $\lambda_i$;

means firstly for combining successive signals delivered by the quantum detector $S(\lambda_i)$, i=0, ..., n in such a manner as to isolate the spectral absorption of the fuel components in each wavelength interval ($\lambda_i;\lambda_{i+1}$); and means for comparing the above-obtained signal combinations with signal combinations obtained previously during a calibration step on a reference gas of known composition, and secondly for deducing the calorific value of a gas.

24. Apparatus according to claim 23, in which the means for combining the signals delivered by the quantum detector for each of the positions of the absorption front corresponding to the successive wavelengths $\lambda_0, \ldots, \lambda_n$ are constituted by means for taking the difference $S(\lambda_{i+1})-S(\lambda_i)$ between said signals taken in consecutive pairs.

25. Apparatus according to claim 23, in which the means for combining the signals delivered by the quantum detector for each of the positions of the absorption front corresponding to the successive wavelengths $\lambda_0$ and $\lambda_1$ are constituted by means for taking the ratio $S(\lambda_{i+1})/S(\lambda_i)$ of said signals taken in consecutive pairs.

26. Apparatus for measuring the energy of electromagnetic radiation, the apparatus comprising:

at least one source for emitting said electromagnetic radiation over a determined spectral range;

a quantum type detector for filtering said electromagnetic radiation and for detecting said electromagnetic radiation and delivering an electrical signal representative of the measure of the energy of said electromagnetic radiation.

27. Apparatus according to claim 26, in which the quantum detector presents a spectral sensitivity having an absorption front at a given wavelength that corresponds to the bandgap of said detector and delivering a signal corresponding to the electromagnetic energy received by said quantum detector, the apparatus further comprising:

means for moving the absorption front of the spectral sensitivity of the quantum detector from a position corresponding to a wavelength $\lambda_0$ towards a position corresponding to a wavelength $\lambda_1$, both of which wavelengths are included in the spectral range of the emitted electromagnetic radiation; and means for combining the signals delivered by the quantum detector for each of the positions of the absorption front corresponding to the wavelengths $\lambda_0$ and $\lambda_1$, and for deducing therefrom the measure of the energy of said electromagnetic radiation in the wavelength interval lying between $\lambda_0$ and $\lambda_1$.

28. Apparatus according to claim 23, in which the means for moving the absorption front are constituted by means for varying a physical parameter on which the position of said absorption front depends.

29. Apparatus according to claim 28, in which the physical parameter is temperature and the means for varying the temperature of the quantum detector comprise an element powered by a variable electricity source and using Peltier effect junctions with which said quantum detector is maintained in thermal contact together with a thermometer element associated with said quantum detector.

* * * * *